United States Patent

Wu et al.

[11] Patent Number: 5,856,608
[45] Date of Patent: Jan. 5, 1999

[54] HYDROTREATING CATALYST COMPOSITION AND PROCESSES THEREFOR AND THEREWITH

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 803,909

[22] Filed: Feb. 21, 1997

[51] Int. Cl.[6] .............................. C07C 2/66; C07C 4/12; C07C 4/18
[52] U.S. Cl. ..................... 585/466; 585/400; 585/446; 585/467; 585/483; 585/486; 585/488; 585/489
[58] Field of Search ...................... 585/400, 483, 585/486, 488, 489, 446, 466, 467

[56] References Cited

U.S. PATENT DOCUMENTS

| | | |
|---|---|---|
| 3,317,622 | 5/1967 | Hoertz, Jr. et al. . |
| 3,729,521 | 4/1973 | Gutberlet et al. . |
| 3,875,081 | 4/1975 | Young . |
| 4,078,990 | 3/1978 | Brennan et al. ............ 208/64 |
| 4,137,147 | 1/1979 | Franck et al. . |
| 4,150,061 | 4/1979 | Feinstein et al. . |
| 4,162,214 | 7/1979 | Maslyansky et al. ........... 585/471 |
| 4,172,813 | 10/1979 | Feinstein et al. ............ 585/475 |
| 4,341,622 | 7/1982 | Tabak et al. ............... 208/66 |
| 4,518,485 | 5/1985 | LaPierre et al. ............ 208/89 |
| 4,676,887 | 6/1987 | Fischer et al. ............. 208/61 |
| 4,919,789 | 4/1990 | Fischer et al. ............. 208/61 |
| 5,004,854 | 4/1991 | Yan ........................ 585/489 |
| 5,011,593 | 4/1991 | Ware et al. ............... 208/213 |
| 5,401,389 | 3/1995 | Mazzone et al. ............ 208/89 |
| 5,409,595 | 4/1995 | Harandi et al. ............ 208/60 |
| 5,411,658 | 5/1995 | Chawla et al. ............. 208/89 |
| 5,689,026 | 11/1997 | Wu et al. ................. 585/489 |

*Primary Examiner*—Elizabeth D Wood
*Attorney, Agent, or Firm*—Lucas K. Shay

[57] ABSTRACT

A catalyst composition and a process for converting a $C_9+$ aromatic compound such as, for example, 1,2,4-trimethylbenzene to a $C_6$ to $C_8$ aromatic hydrocarbon such as a xylene are disclosed. The composition comprises a zeolite, a metal oxide, and optionally a selectivity modifier selected from the group consisting of silicon, sulfur, phosphorus, boron, magnesium, tin, titanium, zirconium, germanium, indium, lanthanum, cesium, oxides thereof and combinations of any two or more thereof. The process comprises contacting a fluid which comprises a $C_9+$ aromatic compound with the catalyst composition under a condition sufficient to effect the conversion of a $C_9+$ aromatic compound to a $C_6$ to $C_8$ aromatic hydrocarbon.

14 Claims, No Drawings

HYDROTREATING CATALYST COMPOSITION AND PROCESSES THEREFOR AND THEREWITH

FIELD OF THE INVENTION

This invention relates to a catalyst composition useful for converting a $C_9+$ aromatic compound to a $C_6$ to $C_8$ aromatic hydrocarbon, to a process for producing the composition, and to a process for using the composition for converting a $C_9+$ aromatic compound to a $C_6$ to $C_8$ aromatic hydrocarbon.

BACKGROUND OF THE INVENTION

It is well known to those skilled in the art that aromatic hydrocarbons are a class of very important industrial chemicals which find a variety of uses in petrochemical industry. It is also well known to those skilled in the art that catalytically cracking gasoline-range hydrocarbons produces aromatic hydrocarbons such as, for example, benzene, toluene, and xylenes (hereinafter collectively referred to as BTX) in the presence of catalysts which contain a zeolite. The product of this catalytic cracking process contains a multitude of hydrocarbons including unconverted $C_5+$ alkanes, $C_5+$ alkenes, $C_5+$ cycloalkanes, or combinations of two or more thereof; lower alkanes such as methane, ethane, and propane; lower alkenes such as ethylene and propylene; and $C_9+$ aromatic compounds. Recent efforts to convert gasoline to more valuable petrochemical products have therefore focused on improving the conversion of gasoline to more valuable aromatic hydrocarbons in the presence of zeolite catalysts. For example, a gallium-promoted zeolite ZSM-5 has been used in the so-called Cyclar Process to convert a hydrocarbon to BTX. The aromatic hydrocarbons can be useful feedstocks for producing various organic compounds and polymers. However, heavier, less useful, aromatic compounds having 9 or more carbon atoms per molecule (hereinafter collectively referred to as $C_9+$ aromatic compounds) are also produced by the conversion process.

Accordingly, there is an ever-increasing need to develop a catalyst, a process for producing the catalyst, and for converting these heavier and less useful aromatic compounds to the more valuable BTX hydrocarbons by a hydrodealkylation process or a transalkylation process in which the feed stream comprising $C_9+$ aromatic compounds also comprise benzene, toluene, a xylene, or combinations of two or more thereof. Such development would also be a significant contribution to the art and to the economy.

SUMMARY OF THE INVENTION

An object of this invention is to provide a catalyst composition which can be used to convert a $C_9+$ aromatic compound to a $C_6$ to $C_8$ aromatic hydrocarbon. Also an object of this invention is to provide a process for producing the catalyst composition. Another object of this invention is to provide a process which can employ the catalyst composition to convert $C_9+$ aromatic compounds to $C_6$ to $C_8$ aromatic compounds. An advantage of the catalyst composition is that it exhibits high hydrodealkylation or transalkylation activity, satisfactory yield of xylenes and BTX, and good stability. Other objects and advantages will become more apparent as this invention is more fully disclosed hereinbelow.

According to a first embodiment of the present invention, a composition which can be used as a catalyst for converting a $C_9+$ aromatic compound to a $C_6$ to $C_8$ aromatic hydrocarbon is provided. The composition is a metal-promoted zeolite, preferably having incorporated therein a selectivity modifier wherein the metal is selected from the group consisting of chromium, cobalt, molybdenum, nickel, rhodium, palladium, platinum, rhenium, tungsten, and combinations of any two or more thereof.

According to a second embodiment of the invention, a process for producing a composition which can be used as catalyst in a hydrodealkylation or transalkylation process is provided. The process for producing such a composition comprises, consists essentially of, or consists of (1) optionally contacting a zeolite, which can be optionally calcined before being contacted, with a compound containing an exchangeable ammonium ion to prepare an ammonium-exchanged zeolite; (2) optionally drying the ammonium-exchanged zeolite; (3) contacting a zeolite or the ammonium-exchanged zeolite with a metal compound, and optionally in the presence of a selectivity modifier, under a condition sufficient to incorporate the metal compound into the zeolite to form a modified zeolite wherein the metal of the metal compound is selected from the group consisting of chromium, cobalt, molybdenum, nickel, rhodium, palladium, platinum, rhenium, tungsten, and combinations of any two or more thereof; the selectivity modifier precursor is selected from the group consisting of phosphorus-containing compounds, sulfur-containing compounds, boron-containing compounds, silicon-containing compounds, magnesium-containing compounds, tin-containing compounds, titanium-containing compounds, zirconium-containing compounds, germanium-containing compounds, indium-containing compounds, lanthanum-containing compounds, cesium-containing compounds, and combinations of any two or more thereof; and (4) contacting the modified zeolite with steam under a condition sufficient to effect the conversion of the metal compound to its corresponding metal oxide wherein the amount of the selectivity modifier precursor is the amount that is sufficient to increase the xylene selectivity as compared to a zeolite having no selectivity modifier incorporated therein.

According to a third embodiment of the present invention, a process which can be used for converting a $C_9+$ aromatic compound to a $C_6$ to $C_8$ aromatic compound is provided which comprises, consists essentially of, or consists of, contacting a fluid which comprises a $C_9+$ aromatic compound, optionally in the presence of benzene, toluene, or xylene, or combinations thereof and further optionally in the presence of an inert fluid or a hydrogen-containing fluid, with a catalyst composition which is the same as disclosed above in the first embodiment of the invention, and can be produced by the process disclosed above in the second embodiment of the invention under a condition effective to convert a $C_9+$ aromatic compound to an aromatic hydrocarbon containing 6 to 8 carbon atoms per molecule.

DETAILED DESCRIPTION OF THE INVENTION

According to the first embodiment of the invention, a composition which can be used as catalyst in a hydrodealkylation or transalkylation process for converting a $C_9+$ aromatic compound to a $C_6$ to $C_8$ aromatic hydrocarbon is provided. The composition can comprise, consist essentially of, or consist of, a metal-promoted zeolite optionally having incorporated therein, or impregnated thereon, a selectivity modifier selected from the group consisting of silicon, phosphorus, sulfur, boron, magnesium, tin, titanium, zirconium, germanium, indium, lanthanum, cesium, oxides thereof, and combinations of any two or more thereof wherein the selectivity modifier is present in the composition in a xylene selectivity-improving amount to improve the selectivity to xylenes when the composition is used in a hydrodealkylation or transalkylation process.

The metal as well as the selectivity modifier can be, and generally is, chemically bonded to oxygen or sulfur. Metal oxides or sulfides can be reduced to metal using a reducing agent.

Any zeolite, or combinations of two or more different zeolites, which is known to one skilled in the art as being capable of catalyzing a hydrodealkylation or transalkylation of a $C_9+$ aromatic compound to a $C_6$ to $C_8$ aromatic hydrocarbon, can be employed in the present invention. The presently preferred zeolite is a zeolite having a surface area, as determined by the BET method using nitrogen, in the range of from about 50 to about 1000 preferably 50 to 500 $m^2/g$; a total pore volume in the range of from about 0.1 to about 2.0, preferably 0.1 to 1.0 ml/g; and an average micropore diameter in the range of from about 0.1 to about 500 Å. The presently preferred zeolite for a hydrodealkylation is a Y-zeolite. The presently preferred zeolite for transalkylation is a beta zeolite, especially the one having a framework topology identified as BEA for it it is highly acidic and shape-selective.

Any metal oxide that, when incorporated into a zeolite, is capable of promoting the hydrodealkylation of a $C_9+$ aromatic compound to a $C_6$ to $C_8$ aromatic hydrocarbon can be employed in the invention. Presently, it is preferred that the metal it is selected from the group consisting of molybdenum, chromium, cobalt, nickel, rhodium, palladium, platinum, rhenium, tungsten, oxides thereof, and combinations of any two or more thereof wherein the oxidation state of the metal can be any available oxidation state. For example, in the case of a molybdenum oxide, the oxidation state of molybdenum can be 0, 2, 3, 4, 5, 6, or combinations of any two or more thereof. The presently preferred metal-promoted zeolite is a Mo—Co/Y zeolite which denotes a zeolite promoted with both molybdenum (oxide) and cobalt (oxide). The presently more preferred metal (oxide) is a combination of molybdenum(VI) (oxide) and cobalt(II) (oxide). These metal (oxide)-promoted zeolites can be produced by any methods known to one skilled in the art. However, it is preferred they be produced by the process disclosed in the second embodiment of the invention. The weight percent (%) of a metal (oxide) in the catalyst composition can be any weight % so long as such weight % can be effective on a hydrodealkylation process. The weight % can generally be in the range of from about 0.01% to about 60%, preferably about 0.1 to about 50%, and most preferably 0.1 to 40%. If a combination of metals or metal oxides is employed, the molar ratio of the second metal, or the third metal, or the fourth metal to the first metal can be in the range of about 0.01:1 to about 100:1.

According to the first embodiment of the invention, the weight ratio of the selectivity modifier to the metal-promoted zeolite can be any ratio so long as the ratio can improve the selectivity to a xylene when the composition is used in a hydrodealkylation or a transalkylation process for converting of a $C_9+$ aromatic compound to a $C_6$ to $C_8$ aromatic hydrocarbon. Generally, the ratio can be in the range of from about 0.0001:1 to about 10:1, preferably about 0.0005:1 to about 10:1, more preferably about 0.001:1 to about 5:1 and most preferably from 0.005:1 to 2:1. Alternatively, the selectivity modifier can be present in the catalyst composition in the range of from about 0.01 to about 50, preferably about 0.05 to about 50, more preferably about 0.1 to about 45, and most preferably 0.1 to 33 grams per 100 grams of the catalyst composition.

According to the present invention, any selectivity modifier that, as compared to use of a metal-promoted zeolite only, can effect the increase in the yield of BTX or a xylene, or the increase in selectivity to a xylene, in the conversion of a $C_9+$ aromatic compound to a $C_6$ to $C_8$ aromatic hydrocarbon can be employed. Presently it is preferred that the selectivity modifier be selected from the group consisting of sulfur, silicon, phosphorus, boron, magnesium, tin, titanium, zirconium, germanium, indium, lanthanum, cesium, oxides thereof, and combinations of any two or more thereof. The presently preferred selectivity modifier is phosphorus or a phosphorus oxide.

Any methods known to one skilled in the art for incorporating a compound or a portion thereof into a zeolite such as, for example, impregnation or extrusion can be employed for producing the composition of the present invention. However, it is presently preferred the composition be produced by the process disclosed in the second embodiment of the invention.

According to the second embodiment of the invention, a zeolite, preferably a Y zeolite for a hydrodealkylation or a beta zeolite for a transalkylation process, can be first contacted with one or more suitable binders in a liquid, preferably aqueous medium, to form a zeolite-binder mixture. Any binders known to one skilled in the art for use with a zeolite are suitable for use herein. Examples of suitable binder include, but are not limited to, clays such as for example, kaolinite, halloysite, vermiculite, chlorite, attapulgite, smectite, montmorillonite, illite, saconite, sepiolite, palygorskite, diatomaceous earth, and combinations of any two or more thereof; aluminas such as for example α-alumina and γ-alumina; silicas; alumina-silica; aluminum phosphate; aluminum chlorohydrate; and combinations of any two or more thereof. Because these binders are well known to one skilled in the art, description of which is omitted herein. The weight ratio of a zeolite to a binder can be in a wide range and generally in the range of from about 200:1 to about 0.01:1, preferably 100:1 to 0.1:1.

The zeolite and the binder can be well mixed by any means known to one skilled in the art such as stirring, blending, kneading, or extrusion, following which the zeolite-binder mixture can be dried in air at a temperature in the range of from about 50° to about 200° C., preferably about 75° to about 175° C., and most preferably 100° to 150° C. for about 0.5 to about 50 hours, preferably about 1 to about 30 hours, and most preferably 1 to 20 hours, preferably under atmospheric pressure. Thereafter, the dried, zeolite-binder mixture can be further calcined in air at a temperature in the range of from about 300° to 1000° C., preferably about 350° to about 750° C., and most preferably 450° to 650° C. to prepare a calcined zeolite-binder. If a binder is not desired, a zeolite can also be calcined under similar conditions to remove any contaminants, if present.

A zeolite, a calcined zeolite, or a calcined zeolite-binder can be treated with a compound containing an exchangeable ammonium ion to prepare an ammonium-exchanged zeolite. Whether a zeolite is calcined or contains a binder, the process or treatment in the second embodiment is the same for each. For the interest of brevity, only a zeolite is described hereinbelow. Examples of suitable ammonium-containing compound include, but are not limited to, ammonium sulfate, ammonium chloride, ammonium nitrate, ammonium bromide, ammonium fluoride, and combinations of any two or more thereof. Treatment of the zeolite replaces the original ions such as, for example, alkali or alkaline earth metal ions of the zeolite with predominantly ammonium ions. Techniques for such treatment are well known to one skilled in the art such as, for example, ion exchange with the original ions. For example, a zeolite can be contacted with a solution containing a salt of the desired replacing ion or ions.

Generally, a zeolite can be suspended in an aqueous solution of an ammonium-containing compound. The concentration of the zeolite-binder in the aqueous solution can be in the range of from about 0.01 to about 200, preferably about 0.1 to about 150, more preferably about 1 to about 100, and most preferably 5 to 75 grams per liter. The amount of the ammonium-containing compound required depends on the amount of the original ion(s) to be exchanged. Upon the preparation of the solution, the solution can be subject to a temperature in the range of from about 30° C. to about 200° C., preferably about 40° C. to about 150° C., and most preferably 50° C. to 125° C. for about 1 to about 100 hours, preferably about 1 to about 50 hours, and most preferably 2 to 25 hours depending on desired degrees of ion exchange. The treatment can be carried out under a pressure in the range of from about 1 to about 10 atmospheres (atm), preferably about 1 atm or any pressure that can maintain the required temperature. Thereafter, the treated zeolite-binder can be washed with running water for 1 to about 60 minutes followed by drying and calcining to produce calcined zeolite. The drying and calcining processes can be carried out substantially the same as those disclosed above for the preparation of a calcined zeolite or zeolite-binder.

Generally, the ammonium-exchanged zeolite becomes hydrogen exchanged upon calcination or high temperature treatment such that a predominant proportion of its exchangeable cations are hydrogen ions. The above-described ion exchanges of exchangeable ions in a zeolite is well known to one skilled in the art. See, for example, U.S. Pat. No. 5,516,956, disclosure of which is incorporated herein by reference. Because the ion exchange procedure is well known, the description of which is omitted herein for the interest of brevity.

A zeolite, with or without a binder, calcined or not, is generally first mixed, with a metal compound which can be converted, in the next step of the process, to a metal oxide upon air calcination or steam treatment. In this step, a modified zeolite is produced. The metal of a suitable metal compound is selected from the group consisting of chromium, cobalt, molybdenum, nickel, rhodium, rhenium, palladium, platinum, tungsten, and combinations of any two or more thereof. The metal compound can be dissolved in a solvent before being contacted. The metal compound, if possible, is preferably in an aqueous solution. The contacting can be carried out at any temperature. Generally, the temperature can be in the range of from about 15° C. to about 100° C., preferably about 20° C. to about 100° C., and most preferably 20° C. to 60° C. under any pressure, preferably atmospheric pressure, for any length of time so long as the metal compound and the zeolite are well mixed, generally about 1 minute to about 15 hours, preferably about 1 minute to about 5 hours. The quantity of metal compound can be any quantity so long as the quantity can result in the composition disclosed in the first embodiment of the invention.

Examples of suitable metal compounds include, but are not limited to, molybdenum(II) acetate, ammonium molybdate, ammonium dimolybdate, ammonium heptamolybdate, ammonium phosphomolybdate, molybdenum(III) bromide, molybdenum(II) chloride, molybdenum(III) chloride, molybdenum(IV) chloride, molybdenum(V) chloride, molybdenum(IV) sulfide, sodium molybdate, potassium molybdate, molybdenum oxychloride, molybdenum fluoride, molybdenum(VI) tetrachloride oxide, ammonium tetrathiomolybdate, bis (acetylacetonate)dioxomolybdenum(VI), chromium(II) acetate, chromium(III) acetate, chromium(III) acetylacetonate, chromium(II) chloride, chromium(III) chloride, chromium(II) fluoride, chromium(III) fluoride, chromium hexacarbonyl, chromium(III) nitrate, chromium nitride, chromium(III) 2,4-pentanedionate, chromium(III) perchlorate, chromium(III) potassium sulfate, chromium (III) sulfate, chromium(III) telluride, cobalt(II) acetate, cobalt(II) acetylacetonate, cobalt(III) acetylacetonate, cobalt (II) benzoylacetonate, cobalt(II) bromide, cobalt(II) carbonate, cobalt(II) chloride, cobalt(II) 2-ethylhexanoate, cobalt(II) fluoride, cobalt(III) fluoride, cobalt(II) iodide, cobalt(II) iodide, cobalt(II) 2,3-naphthalocyanine, cobalt(II) nitrate, cobalt(II) oxalate, cobalt(II) perchlorate, cobalt(II) phthalocyanine, cobalt(II) sulfate, cobalt(II) thiocyanate, cobalt(II) tungstate, nickel(II) acetate, nickel(II) acetylacetonate, nickel(II) bromide, nickel(II) carbonate, nickel(II) chloride, nickel(II) nitrate, nickel(II) perchlorate, nickel phosphide, nickel(II) sulfate, nickel sulfide, nickel(II) titanate, palladium(II) acetate, palladium(II) acetylacetonate, palladium(II) bromide, palladium(II) iodide, palladium(II) nitrate, palladium(II) sulfate, palladium(II) sulfide, rhodium(II) acetate, rhodium(III) acetylacetonate, rhodium(III) bromide, rhodium(III) chloride, rhodium(III) nitrate, rhodium(II) octanoate, rhodium(III) phosphate, rhodium(III) sulfate, tungsten(V) bromide, tungsten(IV) chloride, tungsten(VI) chloride, tungsten hexacarbonyl, tungsten(VI) oxychloride, tungsten(IV) sulfide, tungstic acid, and combinations of any two or more thereof.

The presently preferred metal compounds include, but are not limited to, molybdenum(II) acetate, ammonium molybdate, ammonium dimolybdate, ammonium heptamolybdate, ammonium tetrathiomolybdate, ammonium phosphomolybdate, molybdenum(III) bromide, molybdenum(II) chloride, molybdenum(IV) chloride, molybdenum(V) chloride, molybdenum(IV) sulfide, sodium molybdate, potassium molybdate, molybdenum oxychloride, molybdenum fluoride, molybdenum(VI) tetrachloride oxide, bis(acetylacetonate)dioxomolybdenum(VI), cobalt(II) acetate, cobalt(II) acetylacetonate, cobalt(III) acetylacetonate, cobalt(II) benzoylacetonate, cobalt(II) bromide, cobalt(II) carbonate, cobalt(II) chloride, cobalt(II) 2-ethylhexanoate, cobalt(II) fluoride, cobalt(III) fluoride, cobalt(II) iodide, cobalt(II) iodide, cobalt(II) 2,3-naphthalocyanine, cobalt(II) nitrate, cobalt(II) oxalate, cobalt(II) perchlorate, cobalt(II) phthalocyanine, cobalt(II) sulfate, cobalt(II) thiocyanate, cobalt(II) tungstate, and combinations of any two or more thereof in which molybdenum can be in any possible oxidation state, if not indicated. The presently most preferred metal compound are ammonium heptamolybdate and cobalt nitrate for they are readily available and effective.

According to the second embodiment of the present invention, any selectivity modifier precursor which can be converted to a selectivity modifier, as disclosed in the first embodiment of the invention, that, as compared to use of a metal oxide-promoted zeolite only, can effect the improvement of selectivity to a xylene in a hydrodealkylation process can be employed. Generally, a selectivity modifier precursor, if not a liquid, is dissolved in a liquid to form a solution before being mixed or impregnated with a zeolite or a metal (oxide)-promoted zeolite. The amount of a selectivity modifier required is an amount that can increase BTX or xylene yield, or increase the selectivity to a xylene in a hydrodealkylation or transalkylation process. The amount can also be an amount that can result in the composition disclosed in the first embodiment of the invention. The conditions for contacting a zeolite with a selectivity modifier can be the same as the conditions disclosed above for contacting a zeolite with a metal compound.

Presently it is preferred that a selectivity modifier precursor be selected from the group consisting of sulfur-containing compounds, phosphorus-containing compounds, boron-containing compounds, magnesium-containing compounds, tin-containing compounds, titanium-containing compounds, zirconium-containing compounds, germanium-containing compounds, indium-containing compounds, lanthanum-containing compounds, cesium-containing compounds, and combinations of any two or more thereof.

Generally any phosphorus-containing compounds that, when impregnated onto or incorporated into a metal-promoted zeolite can be converted into a phosphorus oxide and are capable of increasing the selectivity to a xylene or xylenes, as compared to the use of the metal-promoted alumina only in a hydrodealkylation process, can be used in the present invention. Examples of suitable phosphorus-containing compounds include, but are not limited to, phosphorus pentoxide, phosphorus oxychloride, phosphoric acid, phosphines having the formula of $P(OR)_3$, $P(O)(OR)_3$, $P(O)(R)(R)(R)$, $P(R)(R)(R)$, and combinations of any two or more thereof wherein R is the same as that disclosed above. The presently most preferred phosphorus-containing compound is phosphoric acid for it is inexpensive and readily available.

Similarly any silicon-containing compounds which can be converted to a silicon oxide that are effective to enhance hydrodealkylation or transalkylation of a $C_9+$ aromatic compound when used with a metal (oxide)-promoted zeolite can be used in the present invention. Examples of suitable silicon-containing compounds can have a formula of $(R)(R)(R)Si(-O_mSi(R)(R)-)_nR$ wherein each R can be the same or different and is independently selected from the group consisting of alkyl radicals, alkenyl radicals, aryl radicals, alkaryl radicals, aralkyl radicals, and combinations of any two or more thereof; m is 0 or 1; and n is 1 to about 10 wherein each radical can contain 1 to about 15, preferably 1 to about 10 carbon atoms per radical. Specific examples of such polymers include, but are not limited to, silicon-containing polymers such as poly(phenylmethylsiloxane), poly(phenylethylsiloxane), poly(phenylpropylsiloxane), hexamethyldisiloxane, decamethyltetrasiloxane, diphenyltetramethyldisiloxane, and combinations of any two or more thereof. Other silicon-containing compounds include organosilicates such as, for example, tetraethyl orthosilicate, tetrabutyl orthosilicate, tetrapropyl orthosilicate, or combination of any two or more thereof. A number of well known silylating agents such as trimethylchlorosilane, chloromethyldimethylchlorosilane, N-trimethylsilylimidazole, N,O-bis(trimethylsilyl)acetamide, N-methyl-N-trimethylsilyltrifluoroacetamie, t-butyldimethylsilylimidazole, N-trimethylsilylacetamide, methyltrimethoxysilane, vinyltriethoxysilane, ethyltrimethoxysilane, propyltrimethoxysilane, (3,3,3-trifluoropropyl)trimethoxysilane, [3-(2-aminoethyl)aminopropyl]trimethoxysilane, cyanoethyltrimethoxysilane, aminopropyltriethoxysilane, phenyltrimethoxysilane, (3-chloropropyl)trimethoxysilane, (3-mercaptopropyl)trimethoxysilane, (3-glycidoxypropyl)trimethoxysilane, vinyltris(β-methoxyethoxy)silane, (γ-methacryloxypropyl)trimethoxysilane, vinylbenzyl cationic silane, (4-aminopropyl)triethoxysilane, [γ-(β-aminoethylamino)propyl]trimethoxysilane, (γ-glycidoxypropyl)trimethoxysilane, [β-(3,4-epoxycyclohexyl)ethyl]trimethoxysilane, (β-mercaptoethyl)trimethoxysilane, (γ-chloropropyl)trimethoxysilane, and combinations of any two or more thereof can also be employed. The presently preferred silicon-containing compounds are tetraethyl orthosilicate and poly(phenylmethyl) siloxane.

According to the present invention, any sulfur-containing compound that can be converted to a sulfur oxide upon calcining can be employed in the present invention. Example of suitable sulfur containing compounds include, but are not limited to, $(RSH)_n$, $RS_nR$, $RS(O)R$, $RS(O)(O)R$, $M_2S$, $SX_z$, $SO_zX_z$, $CO_mS_z$, $M_zH_mSO_4$, or combinations of any two or more thereof wherein each R, m, and n are the same as those disclosed above, z is a number that fills the proper valency of M or X in which M is an alkali metal ion, an alkaline earth metal ion, an ammonium ion, or H, and X is a halogen or hydrogen. Specific examples of sulfur-containing compounds include, but are not limited to, ammonium sulfide, sodium sulfide, ammonium hydrogen sulfate, sodium hydrogen sulfide, potassium hydrogen sulfide, dimethyl disulfide, methyl mercaptan, diethyl disulfide, dibutyl trisulfide, sulfuryl chloride, sulfur monochloride, dinonyl tetrasulfide, hydrogen sulfide, carbon disulfide, carbonyl sulfide, sulfonyl chloride, or combinations of any two or more thereof.

According to the present invention, any boron-containing compound which, upon being incorporated into a metal oxide-promoted zeolite can be converted into a boron oxide can be used in the present invention. Examples of suitable boron-containing compounds include, but are rot limited to boric acid, borane-ammonium complex, boron trichloride, boron phosphate, boron nitride, triethyl borane, trimethyl borane, tripropyl borane, trimethyl borate, triethyl borate, tripropyl borate, trimethyl boroxine, triethyl boroxine, tripropyl boroxine, and combinations of any two or more thereof.

Examples of suitable magnesium-containing compounds include, but are not limited to, magnesium formate, magnesium acetate, magnesium bromide, magnesium bromide diethyl etherate, magnesium chloride, magnesium fluoride, magnesium nitrate, magnesium sulfate, dibutyl magnesium, magnesium methoxide, and combinations of any two or more thereof.

Similarly, examples of suitable tin-containing compound include, but are not limited to, stannous acetate, stannic acetate, stannous bromide, stannic bromide, stannous chloride, stannic chloride, stannous oxalate, stannous sulfate, stannic sulfate, stannous sulfide, and combinations of any two or more thereof.

Examples of suitable titanium-containing compounds include, but are not limited to, titanium zinc titanate, lanthanum titanate, titanium tetramides, titanium tetramercaptides, titanium tetrabutoxide, titanium tetramethoxides, titanium tetraethoxide, titanium tetrapropoxide, titanium tetrachloride, titanium trichloride, titanium bromides, and combinations of any two or more thereof.

Similarly, examples of suitable zirconium-containing compounds include, but are not limited to, zirconium acetate, zirconium formate, zirconium chloride, zirconium bromide, zirconium butoxide, zirconium tert-butoxide, zirconium chloride, zirconium citrate, zirconium ethoxide, zirconium methoxide, zirconium propoxide, and combinations of any two or more thereof.

Examples of suitable germanium-containing compounds include, but are not limited to, germanium chloride, germanium bromide, germanium ethoxide, germanium fluoride, germanium iodide, germanium methoxide, and combinations of any two or more thereof. Examples of suitable indium-containing compounds include, but are not limited to indium acetate, indium bromide, indium chloride, indium fluoride, indium iodide, indium nitrate, indium phosphide, indium selenide, indium sulfate, and combinations of any two or more thereof.

Examples of suitable lanthanum-containing compounds include, but are not limited to, lanthanum acetate, lanthanum carbonate, lanthanum octanoate, lanthanum fluoride, lanthanum chloride, lanthanum bromide, lanthanum iodide, lanthanum nitrate, lanthanum perchlorate, lanthanum sulfate, lanthanum titanate, and combinations of any two or more thereof.

The presently preferred process for incorporating a selectivity modifier and a metal into a zeolite is that the incorporation of the selectivity modifier precursor into the zeolite is carried out simultaneously, or contemporaneously, with the incorporation of a metal compound to form a modified zeolite. More specifically, a selectivity modifier precursor and a metal compound are simultaneously contacted with, or co-impregnated onto, a zeolite. The conditions for carrying out this simultaneous contacting of both a selectivity modifier and a metal compound can be the same as that disclosed above in the contacting of a zeolite with a metal compound.

In the next step, the modified zeolite is subject to treatment with steam under a suitable condition sufficient to effect the conversion of the selectivity modifier precursor and the metal compound to their corresponding oxide form. The modified zeolite can be optionally air dried to remove most moisture content before being steam-treated. Air drying can be carried out at a temperature for about 25° C. to about 150° C. for about 1 minute to about 30 hours under any pressure that can accommodate the temperature. The air-dried modified zeolite can then be treated with a steam. Generally the steam temperature can be in the range of from about 120° C. to about 1500° C., preferably about 200° C. to about 1200° C., and most preferably 250° C. to 1000° C. The treatment period can be as short as 5 minutes to as long as about 30 hours, preferably about 20 minutes to about 25 hours, and most preferably 1 hour to 20 hours, so long as it is sufficient to convert the selectivity modifier precursor and metal compound to their oxide form. The treatment can be carried out under a pressure that accommodate the necessary temperature and can be in the range of from about atmospheric pressure to about 2,000, preferably to about 1,500, and most preferably to 1000 psig.

The composition of the invention then can be, if desired, pretreated with a reducing agent before being used in a hydrodealkylation process. The presently preferred reducing agent is a hydrogen-containing fluid which comprises molecular hydrogen ($H_2$) in the range of from 1 to about 100, preferably about 5 to about 100, and most preferably 10 to 100 volume %. The reduction can be carried out at a temperature, in the range of from about 250° C. to about 800° C. for about 0.1 to about 10 hours preferably about 300° C. to about 700° C. for about 0.5 to about 7 hours, and most preferably 350° C. to 650° C. for 1 to 5 hours.

According to the third embodiment of the present invention, a process useful for converting a $C_9+$ aromatic compound to a $C_6$ to $C_8$ aromatic hydrocarbon comprises, consists essentially of, or consists of contacting a fluid stream comprising a $C_9+$ aromatic compound and, optionally, in the presence of an inert fluid such as, for example, hydrogen-containing fluid, with a catalyst composition under a condition sufficient to effect the conversion of a $C_9+$ aromatic compound to a $C_6$ to $C_8$ aromatic hydrocarbon. The inert fluid can be hydrogen, nitrogen, helium, argon, carbon dioxide, neon, steam, and combinations of any two or more thereof. The presently preferred inert fluid is a hydrogen-containing fluid. The inert fluid can also be fed separately into contact with a $C_9+$ aromatic compound and a catalyst. The catalyst composition can be the same as that disclosed in the first embodiment and can be prepared by the process disclosed in the second embodiment of the invention of the invention.

In a transalkylation process, the fluid stream comprising a $C_9+$ aromatic compound also comprises benzene, toluene, a xylene, ethylbenzene, or combinations of any two or more thereof which can be present in the fluid stream in any weight % so long as the weight % it is sufficient to effect a transalkylation of a $C_9+$ aromatic compound to produce a $C_6$–$C_8$ aromatic hydrocarbon. Generally, the weight % can be in the range of from about 1 to about 90, preferably 10 to about 80, and more preferably about 20 to about 70, and most preferably 30 to 60 weight %. The source of benzene, toluene, a xylene, ethylbenzene for a transalklylation can be any source such as pure benzene, toluene, a xylene, ethylbenzene. The source can also be the BTX fraction obtained from an aromatization of a hydrocarbon, a mixture of hydrocarbon, a gasoline, or combinations of any two or more thereof. Generally, the operation condition for a transalkylation process can be similar to or substantially the same as that for a hydrodealkylation process. The process condition disclosed hereinbelow can be for either hydrodealkylation or transalkylation process.

The term "fluid" is used herein to denote gas, liquid, vapor, or combinations of two or more thereof. The term "$C_9+$ aromatic compound" is referred to, as defined above, unless otherwise indicated, as a substituted aromatic compound containing at least 9 carbon atoms per molecule. Preferably the substituted aromatic compound has the formula of $R'_q Ar$ wherein each $R'$ is a hydrocarbyl radical having 1 to about 15 carbon atoms and is independently selected from the group consisting of alkyl radicals, aryl radicals, alkaryl radicals, aralkyl radicals, alkenyl radicals, and combinations of any two or more thereof, q is a whole number from 1 to 5, and Ar is an aryl group, preferably, a phenyl group. More preferably $R'$ is an alkyl radical having 1 to about 10 carbon atoms and the aromatic compound has 9 to about 16 carbon atoms per molecule. Most preferably the aromatic compound contains 9 to 12 carbon atoms per molecule.

Any fluid which contains a $C_9+$ aromatic compound as disclosed above can be used as the feed for the process of this invention. The origin of this fluid feed is not critical. However, a preferred fluid feed is a $C_9+$ aromatic compound derived from the heavies fraction of a product from a hydrocarbon, in particular gasoline, aromatization reaction. Generally, this heavies fraction contains primarily trimethylbenzenes such as 1,2,3-trimethylbenzene, 1,2,4-trimethylbenzene, and 1,3,5-trimethylbenzene and tetramethylbenzenes such as 1,2,3,4-tetramethylbenzene, 1,2,3,5-tetramethylbenzene and 1,2,4,5-tetramethylbenzene. Additionally, n-propylbenzene, 3-ethyltoluene, 4-ethyltoluene, 3-n-propyltoluene, 4-n-propyltoluene, and 1,3-diethylbenzene can also be present in the fluid. In a hydrodealkylation process, benzene, toluene, ethylbenzene and xylenes are generally substantially absent from the fluid, i.e., the amount of each of these aromatic hydrocarbons is less than about 0.1 weight %. Thus, there is no significant alkylation of these lower aromatic hydrocarbons by the $C_9+$ aromatic compound, i.e., no significant transalkylation occurs as a side-reaction in the process of this invention. In a transalkylation process, however, benzene, toluene, xylene, ethylbenzene, or combinations of any two or more thereof is generally present in the fluid, as disclosed above.

Any hydrogen-containing fluid which comprises, consists essentially of, or consists of, molecular hydrogen ($H_2$) can be used in the process of this invention. This hydrogen-containing fluid can therefore contain $H_2$ in the range of from about 1 to about 100, preferably about 5 to about 100, and most preferably 10 to 100 volume %. If the $H_2$ content in the fluid is less than 100%, the remainder of the fluid may be any inert gas such as, for example, $N_2$, He, Ne, Ar, steam, or combinations of any two or more thereof, or any other fluid which does not significantly affect the process or the catalyst composition used therein.

The contacting of a fluid comprising a $C_9+$ aromatic compound, in the presence or absence of a hydrogen-containing fluid, with a catalyst composition can be carried out in any technically suitable manner, in batch, semicontinuous, or continuous process under a condition effective to convert a $C_9+$ aromatic compound to a $C_6$ to $C_8$ aromatic hydrocarbon. Generally, a fluid containing a $C_9+$ aromatic compound, preferably being in the vaporized state, and a hydrogen-containing fluid are introduced into a fixed catalyst bed, or a moving catalyst bed, or a fluidized catalyst bed, or combinations of any two or more thereof by any means known to one skilled in the art such as, for example, pressure, meter pump, and other similar means. The condition can include an hourly space velocity (HSV) of the $C_9+$ aromatic compound fluid stream in the range of about 0.01 to about 100, preferably about 0.05 to about 50, and most preferably 0.1 to 30 g feed/g catalyst/hour. The hydrogen-containing fluid hourly space velocity generally is in the range of about 1 to about 10,000, preferably about 5 to about 7,000, and most preferably 10 to 5,000 $ft^3$ $H_2/ft^3$ catalyst/hour. The preferred molar ratio of $H_2$ to the $C_9+$ aromatic compound can be in the range of from about 0.01:1 to about 20:1, preferably about 0.1:1 to about 10:1, and most preferably 0.5:1 to 5:1. Generally, the pressure can be in the range of from about 30 to about 1000 psig, preferably about 50 to about 750 psig, and most preferably 200 to 600 psig, and the temperature is about 250° to about 1,000° C., preferably about 350° to about 800° C., and most preferably 400° C. to 650° C.

The process effluent generally contains a heavies fraction of unconverted $C_9+$ aromatics and other heavy ($C_9+$) aromatic compounds which may have been formed by side-reactions (such as isomerization); a lights fraction of alkanes, mainly methane, ethane, propane, n-butane, isobutane, and minor amounts (about 0.1 to about 5 weight %) of $C_5$ and $C_6$ alkanes such as, for example, isopentane and n-pentane; and a BTX aromatic hydrocarbons fraction (benzene, toluene, ortho-xylene, meta-xylene and para-xylene). Generally, the effluent can be separated into these principal fractions by fractionation distillation which is well known to one skilled in the art. The heavies fraction can be recycled to a hydrodealkylation reactor described above, the lights fraction can be used as fuel gas or as a feed for other reactions such as, for example, in a thermal cracking process to produce ethylene and propylene, and the BTX fraction can be further separated into individual $C_6$ to $C_8$ aromatic hydrocarbon fractions. Alternatively, the BTX fraction can undergo one or more reactions either before or after separation to individual $C_6$ to $C_8$ hydrocarbons so as to increase the content of the most desired BTX aromatic hydrocarbon. Suitable examples of such subsequent $C_6$ to $C_8$ aromatic hydrocarbon conversions are disproportionation of toluene (to form benzene and xylenes), transalkylation of benzene and xylenes (to form toluene), and isomerization of meta-xylene and/or ortho-xylene to para-xylene.

After the catalyst composition has been deactivated by, for example, coke deposition or feed poisons, to an extent that the feed conversion and/or the selectivity to the most valuable $C_6$ to $C_8$ aromatic product (generally xylenes) have become unsatisfactory, the catalyst composition can be reactivated by any means known to one skilled in the art such as, for example, calcining in air to burn off deposited coke and other carbonaceous materials, such as oligomers or polymers, preferably at a temperature of about 400° to about 650° C., followed by a treatment with a reducing agent such as, for example, with hydrogen gas at a temperature of about 400° to about 600° C. The optimal time periods of the calcining and treatment with a reducing agent depend generally on the types and amounts of deactivating deposits on the catalyst composition and on the calcination and reduction temperatures. These optimal time periods can easily be determined by those possessing ordinary skills in the art and are omitted herein for the interest of brevity.

According to the invention, a process which can be used to prepare a catalyst composition is also provided. The process can comprise, consist essentially of, or consist of, contacting a zeolite-containing catalyst with steam under a condition that is sufficient to effect the improvement of the catalyst activity or selectivity to a desired catalytic product. The zeolite-containing catalyst can be a zeolite, or a zeolite having incorporated therein or impregnated thereon a modifier, a promoter, or both. The presently preferred catalyst is a metal oxide-promoted zeolite having incorporated therein a modifier. The metal oxide can be the same as that disclosed above in the previous embodiments of the invention. The modifier can be any modifier so long as it improves the catalyst activity or selectivity to a desired product. The presently preferred modifier is the same as that disclosed above in the previous embodiments of the invention.

The steam treatment of a zeolite-containing catalyst can be carried out under a condition sufficient to effect the production of a catalyst that has the characteristics described immediately above. Generally, the condition can include a temperature in the range of from about 120° C. to 1500° C., preferably about 200° C. to about 1200° C., and most preferably 250° C. to 1000° C.; a contacting period in the range of from about 5 minutes to about 30 hours, preferably about 20 minutes to about 25 hours, and most preferably 1 hour to 20 hours; a pressure in the range of from about 1 atmosphere to about 2,000 psig, preferably to about 1,500 psig, and most preferably to 1,000 psig.

The following examples are presented to further illustrate this invention and are not to be construed as unduly limiting the scope of the present invention.

EXAMPLE I

This example illustrates the preparation of catalyst compositions of the invention and the use of the composition in a hydrodealkylation process.

A Y-zeolite having a designation of Y-84 obtained as 1/16 inch extrudates from UOP Incorporated, Des Plaines, Ill. was used. First, 10 g of the zeolite was impregnated at 25° C. with a Co/Mo/P impregnation solution containing 0.25 g of Co(NO$_3$)$_2$.6H$_2$O, 0.375 g of (NH$_4$)$_6$ Mo$_7$O$_{24}$.4H$_2$O, 0.375 g of H$_3$PO$_4$, and 4 g of H$_2$O by incipient wetness method. The impregnated zeolite, in a U-tube, was steamed at 650° C. for 6 hours to produce 9.81 g of a cobalt, molybdenum-, and phosphorus-promoted zeolite or Co—Mo—P/zeolite containing 0.516 weight % cobalt, 2.07 weight % molybdenum, and 1.028 weight % phosphorus by calculation (catalyst A).

Secondly, 20 g of Y-84 zeolite was well mixed with 200 ml of a 1.0M NH$_4$NO$_3$ aqueous solution at 90° C. The mixture was then heated at 90° C. for 3 hours. Thereafter, the resulting mixture was filtered and dried in air at 125° C. for 16 hours to produce a dried zeolite. The dried zeolite was again mixed with 200 ml of 1.0M NH$_4$NO$_3$ solution at 90° C. and the resulting mixture was again heated at 90° C. for 3 hours and then filtered following this the zeolite was dried at 125° C. (air) for 16 hours to produce 19.36 g of an ammonium-exchanged zeolite. A portion (4.84 g) of the ammonium-exchanged zeolite was then well mixed with 2.73 g of ammonium heptamolybdate in phosphoric acid solution in a jar at 25° C. followed by air drying at 25° C. to no apparent excess moisture and then treating the resulting mixture in a U-tube with a steam at 650° C. for 6 hours to produce 4.70 g of a phosphorus oxide-modified molybdenum oxide-incorporated zeolite containing 2.367 weight % molybdenum and 1.171 weight % phosphorus by calculation (catalyst B). The atomic ratio of P:Mo was 1.531. The ammonium heptamolybdate in phosphoric acid solution contained 7.5 weight % of (NH$_4$)$_6$MO$_7$O$_4$.4H$_2$O, 7.5 weight % of 85% phosphoric acid, and 85 weight % of water.

Thirdly, 10 g of Y-84 zeolite was impregnated with a solution containing 0.25 g of cobalt nitrate (Co(NO$_3$)$_2$.6H$_2$O), 0.375 g of 85% H$_3$PO$_4$, and 4 g of water followed by steam treatment as disclosed above to produce 9.73 g of phosphorus oxide modified, cobalt oxide-promoted zeolite (catalyst C) containing 0.520 weight % of cobalt and 1.036 weight % of phosphorus by calculation (Co/P atomic ratio= 1/3.8)

In a separate run, 10 g of the Y-zeolite was impregnated with a solution containing 0.375 g of ammonium heptamolybdate ((NH$_4$)$_6$MO$_7$O$_4$.4H$_2$O), 0.25 g of Co(NO$_3$)$_2$.6H$_2$O, and 4 g of water as disclosed above. The impregnated zeolite in a U-tube was heated with a steam at 650° C. for 6 hours to produce 9.72 g of cobalt oxide and molybdenum oxide-promoted zeolite (catalyst D). Catalyst D contained 2.096 weight % molybdenum and 0.521 weight % of cobalt by calculation. The Co:Mo atomic ratio of catalyst D was 1:2.5.

In another separate run, 10 grams of Y-84 zeolite was impregnated with 5.0 g of 7.5 weight % (NH$_4$)$_6$Mo$_7$O$_{24}$ solution followed by steam treatment at 650° C. for 6 hours to produce 9.53 g of molybdenum oxide-promoted zeolite (catalyst E). Catalyst E contained 2.138 weight % molybdenum by calculation.

Also in a separate run, 5 g of a Y-zeolite was impregnated with 2.5 g of 7.5 weight % (NH$_4$)$_6$MO$_7$O$_{24}$ by the incipient wetness method followed by air calcination in a muffle furnace at 650° C. for 6 hours to produce 4.81 g of catalyst F. Catalyst F contained 2.118 weight % molybdenum by calcination.

In a further separate run, 11.30 g of the Y-zeolite described above was treated with steam at 650° C. for 6 hours to produce a steamed zeolite. The steamed zeolite was then suspended in a 300 ml of 1.0N NH$_4$NO$_3$—0.1N HNO$_3$ for 16 hours at 95° C. followed by washing with a running water for about 30 minutes. Thereafter, the washed zeolite was dried in air and then calcined in a muffle furnace at 500° C. for 4 hours to produce catalyst G.

These molybdenum oxide-promoted zeolites were then employed, according to the third embodiment of the invention, in a hydrodealkylation process for converting a C$_9$+ aromatic compound to BTX. The liquid feed in the hydrodealkylation runs was heavy C$_9$+ aromatic compounds obtained in a gasoline aromatization process in which gasoline was converted into BTX and C$_9$+ aromatic compounds. The composition of the feed is given in Table I which contained less than 800 ppm S. Not given in Table I are numerous components which were in small quantities and, in some instances, whose chemical structures were unknown.

TABLE I

Composition of Feed

| Feed Component | Weight Percent |
|---|---|
| 1-Methyl-3-ethylbenzene | 2.254 |
| 1-Methyl-4-ethylbenzene | 1.057 |
| 1,3,5-Trimethylbenzene | 1.958 |
| 1-Methyl-2-ethylbenzene | 1.306 |
| 1,2,4-Trimethylbenzene | 9.977 |
| 1,2,3-Trimethylbenzene | 3.060 |
| 1-Methyl-3-i-propylbenzene | 0.286 |
| 2,3-Dihydroindene | 2.845 |
| 1,3-Diethylbenzene | 1.173 |
| 1-Methyl-3-n-propylbenzene | 1.543 |
| 1,4-Diethylbenzeneylbenzene | 0.910 |
| 1-Methyl-4-n-propylbenzene | 0.328 |
| n-Butylbenzene-ethylbenzene | 2.836 |
| 1-Methyl-2-n-propylbenzene | 0.889 |
| 1,4,-Dimethyl-2-ethylbenzene | 1.991 |
| s-C5-benzene/1,3-dimethyl-4-ethylbenzene | 2.958 |
| 1,2-Dimethyl-4-ethylbenzene | 3.454 |
| 1,2-Dimethyl-3-ethylbenzene | 1.007 |
| 1,2,4,5-Tetramethylbenzene | 1.936 |
| 1,2,3,5-Tetramethylbenzene | 2.695 |
| 5-Methylindan | 3.004 |
| 1-Ethyl-2-n-propylbenzene | 1.592 |
| 2-Methylindan | 3.040 |
| 1,3-Di-i-propylbenzene | 1.084 |
| Naphthalene | 4.767 |
| 2-Methylnaphthalene | 3.382 |
| 1-Methylnaphthalene | 1.184 |

A stainless-steel reactor tube (inner diameter 2.5 cm; length 50 cm) was filled with a 20 cm bottom layer of Alundum® alumina (inert, low surface area alumina), one of the catalysts (in 1/16 inch extrudates) in the center position 5 ml, and a 20 cm top layer of Alundum® alumina. The catalysts were pretreated with hydrogen (260 ml/minute) at 575° C. (starting at 25° C. then ramping at 10° C./min) for one hour. The feed was then introduced into the reactor at a rate of 20 milliliters/hour (WHSV or weight hourly space velocity is shown in Table II), together with hydrogen gas at a rate of 260 ml of H$_2$/hours. The reaction temperature was 568° C. to 579° C. as shown in Table II, and the reaction pressure was 500 psig. The reactor effluent was cooled and analyzed with an on-line gas chromatograph at intervals of about 1 hour. The results are shown in Table II.

TABLE II

Y-Zeolite Catalyzed BTX Formation from $C_9$ + Aromatic Compounds

| Catal[a] | wt % | | | Time (hr)[b] | Temp (°C.) | WHSV (hr$^{-1}$) | % Conv $C_9+$[c] | wt % | | Selectivity[e] | |
|---|---|---|---|---|---|---|---|---|---|---|---|
| | Mo | P | Co | | | | | BTX | Xyln's[d] | BTX | Xyln's |
| A | 2.077 | 1.028 | 0.516 | 7.00 | 575 | 5.85 | 77.3 | 58.4 | 20.7 | 0.756 | 0.268 |
| B | 2.367 | 1.171 | 0.000 | 6.95 | 575 | 5.93 | 62.3 | 56.3 | 22.6 | 0.902 | 0.363 |
| C | 0.000 | 1.036 | 0.520 | 6.93 | 571 | 7.23 | 67.1 | 52.9 | 22.3 | 0.788 | 0.333 |
| D | 2.096 | 0.000 | 0.521 | 7.50 | 573 | 6.12 | 67.8 | 53.0 | 22.2 | 0.782 | 0.328 |
| E | 2.138 | 0.000 | 0.000 | 6.80 | 571 | 5.97 | 74.2 | 60.3 | 16.1 | 0.813 | 0.218 |
| F[f] | 2.118 | 0.000 | 0.000 | 7.03 | 574 | 5.81 | 41.6 | 28.8 | 14.2 | 0.692 | 0.342 |
| G | 0.000 | 0.000 | 0.000 | 6.85 | 568 | 6.47 | 16.4 | 9.03 | 4.7 | 0.552 | 0.289 |

[a]Catalyst designation as shown in the text.
[b]Reaction time in hours at which the sample was analyzed.
[c]Conversion of $C_9$ + aromatic compounds.
[d]All isomers of xylene.
[e]Selectivity was calculated by dividing weight % by % conversion of $C_9$ + aromatic compounds.
[f]As shown in the text, catalyst F was air calcined.

The results shown in Table II indicate that treatment with steam (catalyst E) resulted in a more active catalyst than air calcining (catalyst F). The results show that a molybdenum oxide-promoted zeolite (catalyst E) had higher conversion of $C_9+$ aromatic compounds and higher BTX yield than a catalyst which had no Mo incorporation (catalyst G). The results also show that a Mo-promoted zeolite having incorporated therein a phosphorus, or cobalt, or both (catalysts A–C) significantly improved the yield of, as well as selectivity to, BTX or xylenes, as compared to the catalyst produced by merely steaming a Y-zeolite (catalyst G) or steaming a Mo-promoted Y-zeolite (catalyst E). The results further demonstrate that incorporating cobalt into a Mo-promoted zeolite decreased BTX selectivity, but increased xylenes selectivity (catalyst D).

EXAMPLE II

This example illustrates the invention process for preparing catalyst compositions and use of the catalyst compositions in a transalkylation process for converting $C_9+$ aromatic compound to BTX.

A beta zeolite having a framework topology identified as BEA, which was provided by UOP as $\frac{1}{16}$ inch extrudates, was used in this example. First, 10 g of beta zeolite was impregnated with a cobalt nitrate solution containing 0.25 g of $Co(NO_3)_2 \cdot 6\ H_2O$ and 6.25 g of $H_2O$ followed by steam treatment of the resulting cobalt nitrate-impregnated zeolite at 650° C. for 6 hours, similar to the process described in EXAMPLE I, to produce 9.73 g of cobalt-promoted zeolite (catalyst H) which contained 0.520 weight % Co by calculation.

Secondly, 10 g of beta zeolite was co-impregnated with a Co/Mo impregnation solution containing 0.25 g of $Co(NO_3)_2 \cdot 6\ H_2$, 0.375 g of $(NH_4)_6Mo_7O_{24} \cdot 4\ H_2O$, and 6.00 g of $H_2O$. The resulting cobalt nitrate and ammonium molybdate-impregnated zeolite was heated with steam at 650° C. for 6 hours to produce 9.98 g of cobalt- and molybdenum-promoted zeolite (catalyst I) containing 0.507 weight % Co and 2.042 weight % Mo by calculation.

Catalyst J was prepared by impregnating the Co/Mo impregnation described above in producing catalyst I, onto 10 g of beta zeolite and, following the impregnation, the resulting zeolite was air-calcined in a muffle furnace at 538° C. for 6 hours. Catalyst J weighed 10.04 g and contained 2.030 weight % Mo and 0.504 weight % Co.

In a separate run, 10 g of beta zeolite was impregnated with an ammonium molybdate solution containing 0.375 g of $(NH_4)_6Mo_7O_{24} \cdot 4\ H_2O$ and 6.00 g of $H_2O$ to form an ammonium molybdate-impregnated zeolite which was air calcined at 538° C. for 6 hours to produce 10.01 g of catalyst K. Catalyst K contained 2.036 weight % of Mo.

Catalysts H, I, J, and K were then separately used to catalyze a transalkylation reaction of a feed comprising $C_9+$ aromatic compounds and toluene to produce a product containing a higher concentration of BTX than the feed. The composition of aromatic compounds, up to 12 carbon atoms per molecule, of the feed used for the transalkylation it is shown in Table III. There were numerous unidentified components in the feed that are not shown in the calculation disclosed in Table III.

TABLE III

| Composition | Weight % |
|---|---|
| Paraffins | 2.032 |
| i-Paraffins | 9.255 |
| Naphthenes | 1.267 |
| Aromatics | |
| $C_6$ | 0.000 |
| $C_7$ | 50.248 |
| $C_8$ | 0.411 |
| $C_9$ | 11.315 |
| $C_{10}$ | 12.664 |
| $C_{11}$ | 9.457 |
| $C_{12}$ | 3.001 |
| Total | 87.096 |
| Sulfur (ppmw) | 658 |

A stainless-steel reactor tube (inner diameter: 2.5 cm; length: 50 cm) was filled with a 20 cm bottom layer of Alundum® alumina (inert, low surface area alumina, provided by Norton Company, Worcester, Md.), 5 ml of one of the zeolite materials described in Example II, and a 20 cm top layer of Alundum®. The reactor and its content were pre-heated from room temperature to the desired reaction temperature of about 555° C. The zeolite materials (catalysts) were pretreated with flowing hydrogen gas at a rate of 260 ml per minute at 500° C. (starting at 25° C. and ramping at 10° C./min). The reaction pressure was set at 500 psig. A liquid feed as shown in Table III was introduced into the heated reactor at a rate of 20 ml/hour, which was equivalent to a hourly space velocity of about 5.6 ml/ml catalyst/hour. The product, which exited the reactor, was cooled, analyzed by means of an online gas chromatograph at intervals of about 1 hour. Pertinent test results are summarized in Table IV.

TABLE IV

| | | | | | | | | |
|---|---|---|---|---|---|---|---|---|
| CoMo/Zeolite-Catalyzed Transalkylation of Toluene & $C_9$ + Aromatics ||||||||||
| | wt % | | Time | Tem | % Conv | wt % Lts[b] | wt %[c] | Avg wt % |
| Catal[a] | Co | Mo | (hr) | (°C.) | $C_9+$ | $C_1$–$C_6$ | Xyln's | coke/hr[d] |
| H | 0.520 | 0.000 | 7.37 | 552 | 56.7 | 4.6 | 7.6(0.134) | 1.592 |
| I | 0.507 | 2.042 | 7.19 | 555 | 77.9 | 6.9 | 21.6(0.277) | 1.653 |
| J | 0.504 | 2.030 | 7.25 | 550 | 79.7 | 11.6 | 21.7(0.272) | 2.133 |
| K | 0.000 | 2.036 | 6.91 | 552 | 82.0 | 10.4 | 20.2(0.246) | 3.063 |

[a]Catalyst designation; see text for detail.
[b]Weight % of lights ($C_1$–$C_6$ nonaromatic hydrocarbons) in reactor effluent.
[c]Weight % of total xylenes in reactor effluent; the values in the parentheses are selectivity to xylenes measured as described in Table II.
[d]Coke was determined at the end of the reaction by removing the catalysts from the reactor and determined with a thermal gravimetric analyzer (TGA), manufactured by TA Instruments, New Castle, Delaware.

The results in Table IV shows incorporation of molybdenum into a zeolite (catalysts I–K) improved the yield of, and selectivity to, xylenes. The results also show that incorporation of cobalt into a zeolite (catalysts H–J) decreased or suppressed coke formation during the transalkylation reaction. Comparing catalyst I and catalyst J, it can be readily discerned that steam treatment further suppressed coke formation during the transalkylation reaction.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed:

1. A hydrodealkylation process comprising contacting, in the presence of a hydrogen-containing fluid, a fluid comprising a $C_9+$ aromatic compound with a catalyst composition under a condition sufficient to effect the conversion of said $C_9+$ aromatic compound to a $C_6$ to $C_8$ aromatic hydrocarbon wherein said catalyst composition is prepared by the steps comprising: (1) contacting a Y-zeolite with a metal compound, contemporaneously with phosphoric acid, under a condition sufficient to incorporate said metal compound into said Y-zeolite to form a modified zeolite and (2) treating said modified zeolite with steam under a condition sufficient to effect the conversion of said metal compound to its corresponding metal oxide wherein the metal of said metal compound is selected from the group consisting of chromium, cobalt, molybdenum, nickel, rhodium, palladium, platinum, tungsten, and combinations of any two or more thereof.

2. A process according to claim 1 wherein said $C_9+$ aromatic compound has the formula of $R'_qAr$ in which each R' it is a hydrocarbyl radical having 1 to about 15 carbon atoms and it is independently selected from the group consisting of alkyl radicals, aryl radicals, alkaryl radicals, aralkyl radicals, alkenyl radicals, and combinations of any two or more thereof, q it is a whole number from 1 to 5, and Ar it is an aryl group.

3. A process according to claim 1 wherein said metal compound is selected from the group consisting of a molybdenum-containing compound, a cobalt-containing compound, and combinations of any two or more thereof.

4. A process according to claim 1 wherein said metal compound is ammonium heptamolybdate.

5. A process according to claim 1 wherein said metal compound is combination of ammonium heptamolybdate and cobalt nitrate.

6. A process according to claim 1 wherein said metal compound is a combination of ammonium heptamolybdate and cobalt nitrate.

7. A process comprising contacting, in the presence of a hydrogen-containing fluid, a fluid comprising a $C_9+$ aromatic compound with a catalyst composition under conditions effective for converting a $C_9+$ aromatic compound to a $C_6$–$C_8$ aromatic hydrocarbon wherein said catalyst composition is produced by the process comprising: (1) contacting a Y-zeolite with a solution containing a molybdenum-containing compound, a cobalt-containing compound, and phosphoric acid under a condition sufficient to incorporate said molybdenum-containing compound, cobalt-containing compound, and phosphoric acid into said zeolite to form a modified zeolite; and (2) steam-treating said modified zeolite.

8. A process according to claim 7 wherein said molybdenum-containing compound is ammonium heptamolybdate.

9. A process according to claim 7 wherein said cobalt-containing compound is cobalt nitrate.

10. A process according to claim 8 wherein said cobalt-containing compound is cobalt nitrate.

11. A transalkylation process comprising contacting, in the presence of a hydrogen-containing fluid, a fluid comprising a $C_9+$ aromatic compound with a catalyst composition under conditions effective for converting a $C_9+$ aromatic compound to a $C_6$–$C_8$ aromatic hydrocarbon wherein said catalyst composition is produced by the process comprising: (1) contacting a beta zeolite with a solution containing both a molybdenum-containing compound and a cobalt-containing compound under a condition sufficient to incorporate said molybdenum-containing compound and cobalt-containing compound into said zeolite to form a modified zeolite; and (2) steam-treating said modified zeolite.

12. A process according to claim 11 wherein said molybdenum-containing compound is ammonium heptamolybdate.

13. A process according to claim 11 wherein said cobalt-containing compound is cobalt nitrate.

14. A process according to claim 12 wherein said cobalt-containing compound is cobalt nitrate.

* * * * *